United States Patent [19]

Fleming et al.

[11] Patent Number: 5,476,960
[45] Date of Patent: * Dec. 19, 1995

[54] αAMINONITRILES DERIVED FROM REACTION OF CARBONYL COMPOUNDS AND FATTY AKLYL ALKYLENE DIAMINES

[75] Inventors: Alison A. Fleming, Mohegan Lake; Robert F. Farmer, Waccabuc, both of N.Y.; James F. Gadberry, Danbury, Conn.

[73] Assignee: Akzo Nobel N.V., Arnhem, Netherlands

[*] Notice: The portion of the term of this patent subsequent to Jun. 7, 2011, has been disclaimed.

[21] Appl. No.: 224,353

[22] Filed: Apr. 7, 1994

Related U.S. Application Data

[63] Continuation of Ser. No. 10,897, Jan. 29, 1993, Pat. No. 5,319,126.

[51] Int. Cl.[6] .................. C07C 255/30; C07C 255/04; C07C 255/33
[52] U.S. Cl. ............ 558/452; 558/455; 558/390; 558/408; 558/409; 558/430
[58] Field of Search .................. 558/390, 408, 558/409, 430, 452, 455

[56] References Cited

U.S. PATENT DOCUMENTS

| | | | |
|---|---|---|---|
| 2,164,781 | 7/1959 | Platz et al. | 260/534 |
| 3,040,029 | 6/1962 | Poppelsdorf et al. | 558/452 X |
| 3,104,199 | 9/1963 | Langdon et al. | 558/452 X |
| 3,424,783 | 1/1969 | Harper, et al. | 260/465.5 |
| 3,522,620 | 8/1970 | Nozawa et al. | 558/452 X |
| 3,757,010 | 9/1973 | Balzer et al. | 558/452 X |
| 4,404,167 | 9/1983 | Rozenfeld et al. | 558/452 X |
| 4,551,526 | 11/1985 | Mai et al. | 544/163 |
| 5,062,978 | 11/1991 | Weber et al. | 252/49.3 |
| 5,319,126 | 6/1994 | Fleming et al. | 558/452 |

FOREIGN PATENT DOCUMENTS

| | | |
|---|---|---|
| 2442239 | 3/1975 | Germany . |
| 50-94122 | 7/1975 | Japan . |

OTHER PUBLICATIONS

The Condensed Chemical Dictionary, 9th ed (1977), p. 374.
Kirk–Othmer Encyclopedia of Chemical Technology, 4th ed., vol. 2, p. 405 (1982).
Jacobson, "N-Substituted α-Aminoisobutyronitriles from Acetone Cyanohydrin", J.A.C.S., 67; pp. 1996–1998 (1945).
Derwent Patent Abstract, 19642 W/12 [Date Unknown] (Abstract of Ger. Offen. 2,442,239).
"Synthesis and Properties of α-Aminonitriles", Shaftran, et al., Russian Chemical Reviews, 58 (2), pp. 148–162 (1989).
Luten, Jr., "The Preparation of Aminonitriles and Their Quaternary Ammonium Derivatives", J. Org. Chem. 3 (pp. 588–597) (1938–1939).

*Primary Examiner*—Joseph Paul Brust
*Attorney, Agent, or Firm*—Richard P. Fennelly; Louis A. Morris

[57] ABSTRACT

An α-aminonitrile compound derived from the reaction, in the presence of a cyanide source of (1) a bisulfite adduct of a carbonyl compound selected from the group consisting of an aldehyde and a ketone with (2) a fatty alkyl alkylene diamine containing two reactible amino functionalities which is of the formula $RNHR_1NH_2$, where R is fatty alkyl and $R_1$ is lower alkylene of up to six carbon atoms.

1 Claim, No Drawings

α AMINONITRILES DERIVED FROM REACTION OF CARBONYL COMPOUNDS AND FATTY AKLYL ALKYLENE DIAMINES

This is a continuation of U.S. Ser. No. 010,897, filed Jan. 29, 1993, now U.S. Pat. No. 5,319,126.

BACKGROUND OF THE INVENTION

A variety of disclosures exist in the art regarding the syntheses of α-aminonitriles, which contain the characteristic linkage —N—C(CN)—, including the following:

U.S. Pat. No. 4,551,526 to K. H. X. Mai et al. prepares aminonitriles by reacting an aldehyde or ketone with trimethylsilyl cyanide to prepare α-trimethylsilyloxynitrile which is then reacted with a monoamine or water in the presence of a lower alkyl alcohol or water to form the desired α-aminonitrile.

Japanese Patent Publication No. 75/94,122 describes N-alkylglycinonitriles of the general formula

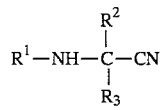

where $R^1$ is $C_{10}$–$C_{20}$ alkyl and $R^2$ and $R^3$ are hydrogen or lower alkyl. The synthesis procedure uses a monoamine reagent.

German Offenlegungsschrift No. 2,442,239 describes α-aminonitriles which also contain a single amino nitrogen radical.

U.S. Pat. No. 2,164,781 to C. Platz et al., although showing α-aminonitriles containing a single amino nitrogen radical, also contains a suggestion that diamines containing a high molecular radical, such as dodecyl, can also be used as a starting reagent and can be reacted with an aldehyde and cyanide source to form the desired α-aminonitrile. This patent mentions dodecyldiethylethylene diamine of the formula

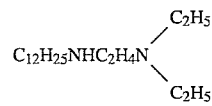

as an example of such a diamine to use.

DESCRIPTION OF THE INVENTION

The present invention relates to α-aminonitrile compounds that are derived from a fatty alkyl alkylene diamine by reaction of such a diamine with a cyanide source and the bisulfite adduct of a carbonyl compound. The terminology "fatty alkyl alkylene diamine" is to be construed as covering diamines of the general formula

where R is fatty alkyl (e.g., $C_{12}$ to $C_{22}$ alkyl) and $R^1$ is alkylene, such as lower alkylene of up to six carbon atoms. The diamines contain two reactive amino functionalities unlike the diamines described in U.S. Pat. No. 2,164,781 where one of the amino functionalities is completely blocked by N-ethyl substitution.

Two classes of α-aminonitriles can be formed (or mixtures thereof) depending upon whether reaction with the carbonyl compound ($R_2C(O)R_3$, where $R_2$ is alkyl or aryl, such as phenyl and $R_3$ is alkyl, aryl, or hydrogen), occurs at either the secondary amine (—N(H)—) or the primary amine (—$NH_2$) functionality (or both). Aldehydes, where $R_3$ is hydrogen, form one class of carbonyl compound which can be used in accordance with the present invention. Ketones which form bisulfite addition products (where $R_3$ is lower alkyl) can also be employed as another class of carbonyl compound herein. Hydroxy functionalized derivatives of the foregoing aldehydes and ketones, the so-called "aldoses" and "ketoses" may also be used.

Reaction at the primary amine yields compounds of the formula

whereas reaction at the secondary nitrogen yields compounds of the formula

where R, $R_1$, $R_2$ and $R_3$ are as previously described and reaction of both primary and secondary nitrogens yields compounds of the formula

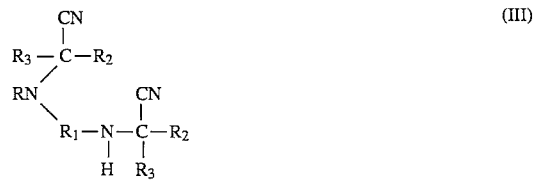

where R, $R_1$, $R_2$ and $R_3$ are as previously described. Compounds of the formulae I and II will be the predominant and desired products of the present invention. By careful control of the stoichiometry, combined with using a diamine containing two amines with differing reactivity, it is possible to obtain, as the major product, the α-aminonitrile from reaction of only the primary amine or the bis(α-aminonitrile) from reaction of both the primary and secondary amines. A 1:1 molar ratio of alkyl alkylene diamine to aldehyde, sodium bisulfite, and alkali cyanide in aqueous media at room temperature will, for example, produce compound I, above, as the major product with less than 20% of compound II being produced. Increasing the molar ratio of alkyl alkylene diamine to aldehyde, sodium bisulfite, or alkali cyanide to 1:2 or 1:3 in aqueous media at room temperature yields compound III exclusively. Any excess aldehyde, sodium bisulfite and cyanide will react together to form cyanohydrin. Therefore, it is desirable to only use a minimal excess of these reagents. It is possible to remove the cyanohydrin by extraction, e.g., in the case of the cyanohydrin formed from isobutyraldehyde, by extraction from the aminonitrile with water.

It is within the scope of the present invention to use reagents other than sodium bisulfite which form a bisulfite adduct with an aldehyde. For example, sodium metabisulfite, also known as sodium pyrosulfite, can be used in place of sodium bisulfite, if desired.

The products described herein have surfactant properties.

The following Examples further illustrate the present invention.

EXAMPLES 1–9

These Examples illustrate the synthesis of a variety of aminonitriles from certain fatty amines and isobutyraldehyde.

The following general synthesis procedure was employed:

The bisulfite adduct of the aldehyde was formed by adding the aldehyde (0.11 mole) to an aqueous solution of bisulfite (0.11 mole in 100 mL $H_2O$). Depending on the aldehyde, the mixture was stirred between 25°–90° C. (Isopropyl alcohol was added if needed to completely dissolve the adduct). After one hour, the amine (0.10 mole) was added either neat or as a solution. (Isopropyl alcohol, toluene, and $CH_2Cl_2$ all work well.) Stirring was continued at room temperature for thirty minutes; then NaCN (0.10 mole) in $H_2O$ (50 mL) was added. Stirring was continued at room temperature until conversion of the amine to the aminonitrile was completed. In most cases, the amine and sodium cyanide were added simultaneously or even in reverse order. The reaction times were typically one-half hour to six hours.

The Table set forth below shows the results obtained with isobutyraldehyde. The following trademarked products comprising amines were used:

ARMEEN 16D: comprises 98% (min.) of hexadecylamine.

ARMEEN 18D: comprises 98% (min.) of octadecylamine.

ARMEEN TD: comprises 98% (min.) of tallowalkylamine.

PRIMENE 81-R: comprises primary $C_{12}$–$C_{14}$ aliphatic amines with highly branched alkyl chains in which the amino nitrogen is linked to a tertiary carbon as in a t-butyl group.

DUOMEEN CD: comprises N-coco-1,3-diaminopropane.

DUOMEEN T: comprises about 75% N-tallow-1,3-diaminopropane and 25% ARMEEN T, a tallowalkyl amine.

The ARMEEN and DUOMEEN brand products are available from Akzo Chemicals Inc. The PRIMENE brand material is available from Rohm and Haas Company.

| Amine | Crude Yield | Product Distribution* |
|---|---|---|
| $C_{12}H_{25}NH_2$[a] | 96% | 96% aminonitrile, 4% amine |
| $C_{14}H_{29}NH_2$[b] | 97% | 87% aminonitrile, 10% amine, 3% acid[d] |
| ARMEEN 16D[b] | 93% | >99% aminonitrile |
| ARMEEN 18D[b] | 96% | 97% aminonitrile, 3% amine |
| ARMEEN TD[a] | 97% | 95% aminonitrile, 5% amine |
| PRIMENE 81R[c] | 88% | 97% aminonitrile, 3% imine |
| DUOMEEN CD[a,e] | 97% | 65% primary amine reacted 16% secondary amine reacted 19% both amines reacted |
| DUOMEEN CD[f] | 98% | both amines completely reacted |
| DUOMEEN T[f] | 87% | both amines completely reacted |

*determined by quantitative $^{13}C$ NMR.
[a] reaction was run on a 0.10 mole scale.
[b] reaction was run on a 0.05 mole scale.
[c] reaction was run on a 0.015 mole scale.
[d] the acid was isobutyric acid.
[e] molar ratios = about 1.
[f] the molar ratio of aldehyde to DUOMEEN CD brand product was 2.0–3.0 and the molar ratio of cyanide to the DUOMEEN CD product was 2.0–3.0.

The synthesis Examples given for the DUOMEEN brand diamines is in accordance with the present invention. The others are presented for comparison purposes only.

EXAMPLES 10–16

The general procedure of Examples 1–9 was used to make aminonitriles from amines and aldehydes as shown below. In the Table, the trademark ARMEEN TD is used on a product commercially produced by Akzo Chemicals Inc. which comprises 97% (min.) of tallowalkylamine.

| Amine | Aldehyde | Crude Yield | Product Distribution |
|---|---|---|---|
| ARMEEN TD[a] | 2-ethylhexanal | 90% | 90.9% aminonitrile, 6.6% amine, 1.3% imine, 1.2% ester[b] |
| ARMEEN 18D[a] | 2-ethylhexanal | 96% | 98.4% aminonitrile, 0.6% imine, 1% ester[b] |
| Tetradecylamine[a] | 2-ethylhexanal | 93% | 97.1% aminonitrile, 0.9% imine, 2.0% ester[b] |
| ARMEEN T[a] | formaldehyde | 99% | 98.7% aminonitrile, 1.3% unidentified secondary amines |
| DUOMEEN CD[d] | 2-ethylhexanal | 98% | both amines completely reacted |
| DUOMEEN CD[c] | 2-ethylhexanal | 98% | 78.4% primary amine reacted 13% secondary amine reacted 8.6% both amines reacted |
| DUOMEEN T[d] | 2-ethylhexanal | 90% | both amines completely reacted. |

[a] reaction was run on a 0.01 mole scale.
[b] ester from oxidation of the aldehyde and reaction with isopropanol.
[c] molar ratios = about 1.
[d] the molar ratios of aldehyde and of cyanide to the amine was 2.0–3.0.

The synthesis Example utilizing the DUOMEEN brand material is in accordance with the present invention. The others are presented for comparison purposes only.

The foregoing Examples, which are presented for illustrative purposes only, should not be construed in a limiting sense. The scope of protection which is sought is set forth in the claims which follow.

We claim:

1. An α-aminonitrile compound formed by the reaction, in the presence of a cyanide source of (1) a bisulfite adduct of a carbonyl compound selected from the group consisting of an aldehyde and a ketone with (2) a fatty alkyl alkylene diamine containing two reactible amino functionalities which is of the formula $RNHR_1NH_2$, where R is fatty alkyl and $R_1$ is lower alkylene of up to six carbon atoms.

* * * * *